United States Patent [19]

Raczkowski et al.

[11] 4,212,390
[45] Jul. 15, 1980

[54] WOUND CLIP RACK

[75] Inventors: Jan Raczkowski, Glendale; Irving A. Speelman, East Williston, both of N.Y.

[73] Assignee: Propper Manufacturing Co., Inc., Long Island City, N.Y.

[21] Appl. No.: 843,715

[22] Filed: Oct. 20, 1977

[51] Int. Cl.² .............................................. B65D 85/00
[52] U.S. Cl. .................... 206/339; 206/341; 206/485; 206/564; 206/592; 211/13
[58] Field of Search ............... 128/325; 206/338–339, 206/341, 443, 477–478, 480, 485–486, 488, 557, 560, 564–565, 591–592; 211/13, 126, 65, 68, 69; 221/312 R, 312 C

[56] References Cited

U.S. PATENT DOCUMENTS

| 1,278,130 | 9/1918 | Freeman | 206/341 |
|---|---|---|---|
| 2,023,220 | 12/1935 | Diamond | 206/341 |
| 2,228,493 | 1/1941 | Will | 211/69 X |
| 3,275,211 | 9/1966 | Hirsch et al. | 227/124 |
| 3,315,863 | 4/1967 | O'Dea | 227/19 |
| 3,363,628 | 1/1968 | Wood | 128/325 |
| 3,713,533 | 1/1973 | Reimels | 128/325 X |
| 4,076,120 | 2/1978 | Carroll et al. | 128/325 X |

OTHER PUBLICATIONS

"Ligaclip Ligating Clips and Appliers, The Locked-in Clip", Ethicon, Inc. 1973.

Primary Examiner—Stephen Marcus
Attorney, Agent, or Firm—Amster, Rothstein & Engelberg

[57] ABSTRACT

A wound clip rack has a base and a plurality of groups of flexible support fingers projecting upwardly from the base. Each group of flexible support fingers is adapted to support one wound clip. Each group includes at least one and preferably two pairs of flexible support fingers, the fingers of each pair being spaced apart from one another and having facing support surfaces.

7 Claims, 5 Drawing Figures

WOUND CLIP RACK

This invention relates generally to an improved rack for supporting and dispensing wound clips which are used by surgeons to close wounds in surgical operations.

Wound clips have long been known in the surgical arts and are often used by surgeons to bind skin under circumstances in which stitches and other techniques for binding wounds are inappropriate. A typical wound clip with which this invention may be used is illustrated in U.S. Pat. No. 2,232,142 of Feb. 18, 1941.

Under most circumstances, it is necessary for a surgeon to use more than one wound clip during a particular surgical procedure. It therefore becomes necessary to provide the surgeon with a supply of wound clips packaged and arrayed in such a manner that the surgeon can remove the wound clips from the rack in rapid succession and use them under demanding time pressures.

Wound clip racks of various types have been used in the past, as can be seen, for example, in U.S. Pat. No. 3,713,533. In general, such racks must maintain the wound clips in a position such that the clips can be readily removed by the surgeon with the appropriate instrument and, where wound clips are of the type which have sharp points (as is the case with the wound clips disclosed in the aforementioned U.S. Pat. No. 2,232,142), they must be supported in such a way that the sharp points will not be exposed to those handling the loaded wound clip rack.

Various problems have existed up to now with prior wound clips racks. One such problem is that once other wound clip racks have been loaded with wound clips, it becomes difficult to sterilize the clips properly. This is because most such clip and rack arrangements do not leave the wound clips sufficiently exposed to permit adequate circulation of sterilizing gas. Similarly, with certain wound clip racks, it has been necessary to sterilize the wound clips immediately prior to use.

Further, previous racks either mount the wound clips so securely that it is difficult or awkward to remove them, or mount the wound clip so loosely that there is a risk of the wound clips separating from the rack before they are intentionally removed. A related problem has been that prior wound clip racks do not lend themselves to being loaded by hand without considerable difficulty, since it is ordinarily necessary for the worker mounting the clips to watch what he is doing very closely and to exercise great care in loading the clips properly.

Still another problem with existing wound clip racks has been that they do not accommodate more than one size of wound clip, thus necessitating the production of racks of various sizes.

Accordingly, it is an object of the present invention to provide a wound clip rack which will allow the wound clips to be thoroughly sterilized after they have been mounted on the rack.

It is a further object of the present invention to provide a wound clip rack which will retain the wound clips securely enough to prevent accidental removal, but which will present the wound clips in a position to be easily removed by the user with the appropriate instrument.

It is another object of the invention to provide a wound clip rack which can be loaded by hand without close visual control.

It is yet another object of the invention to provide a wound clip rack which can be used with wound clips of a variety of different widths.

In accordance with an illustrative embodiment demonstrating objects and features of the present invention, a rack adapted to support and dispense wound clips includes a base with a plurality of groups of flexible support fingers projecting upwardly from the base, one group of flexible support fingers for each wound clip to be supported on the rack. Each group includes at least one pair of flexible support fingers, with the fingers of each pair being spaced apart from one another and having facing support surfaces. The support surfaces include support shelves which are adapted to grasp and hold a wound clip. A groove is provided in the base to receive and protect the points of the wound clip.

The above description as well as further objects, features and advantages of the present invention will be more fully understood by reference to the following detailed description of the presently preferred, but nonetheless illustrative embodiment in accordance with the present invention, when taken in conjunction with the accompanying drawings wherein.

Figure 1:
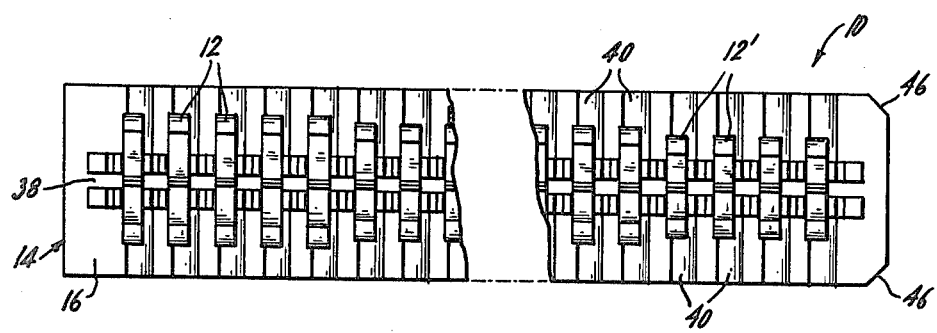
FIG. 1 is a broken top view of a preferred embodiment of a wound clip rack of the present invention wherein the rack is loaded with wound clips of various widths to illustrate how the present invention can accommodate various sizes of wound clips.

Referring now to the figures, and in particular to FIG. 1, it will be seen that the wound clip rack, referred to generally as 10, is adapted to receive a plurality of wound clips 12.

Figure 4:
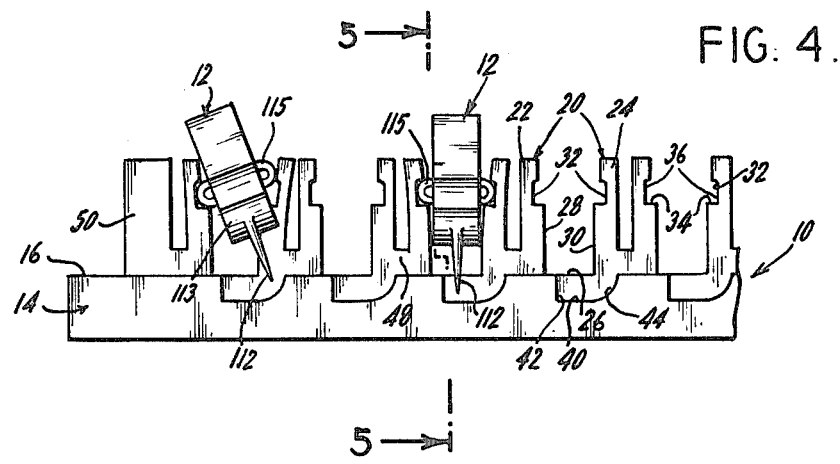
FIG. 4 is a broken side view of the rack showing one wound clip at an intermediate stage of loading and another wound clip in fully loaded position.
Figure 5:
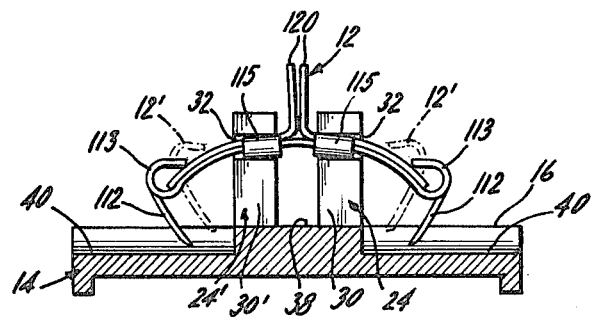
FIG. 5 is a sectional view taken along the line 5—5 in FIG. 4 and looking in the direction of the arrows, showing a cross section of a portion of the wound clip rack with a wound clip of one width mounted in the rack and a wound clip of a second width shown in phantom.

The structure of a wound clip which can be used most advantageously with the rack of the instant invention can best be seen in FIGS. 4 and 5. Wound clips 12 typically have cylindrical end members 113, prongs 112, saddle-like reinforcing members 115 and upset tabs 120. Wound clips 12 are inserted in the skin by squeezing cylindrical end members 113 together with an appropriate instrument, which brings prongs 112 close together to bind a wound and causes upset tabs 120 to spread apart. The wound clip 12 is removed by squeezing the upset tabs 120 together, which causes the prongs 112 to spread apart and substantially return to their initial position.

Figure 2:
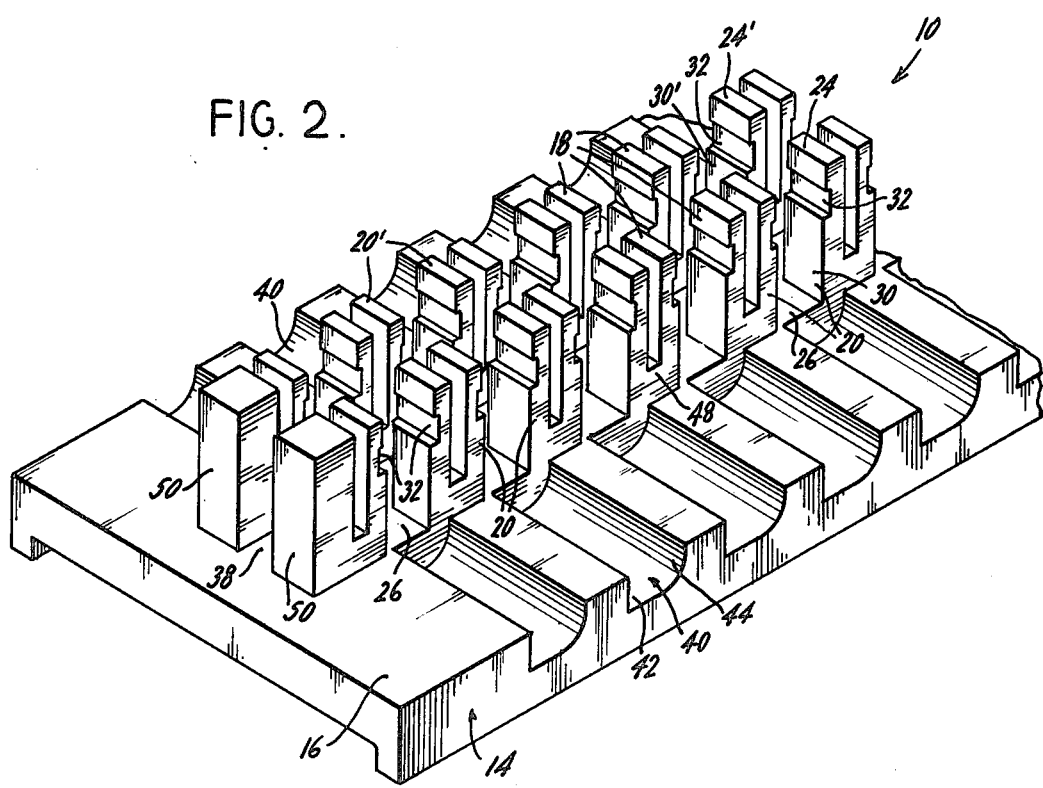
FIG. 2 is a broken perspective view of the rack.

As seen in FIG. 2, the wound clip rack 10 has a base 14 with a top surface 16. A plurality of groups 18 of flexible support fingers project upwardly from base 14. Each group 18 has two pairs 20 and 20' of flexible support fingers. The individual flexible support fingers 22 and 24 of pair 20 are spaced apart from one another defining a gap 26, while fingers 22' and 24' are spaced apart defining gap 26'.

Pair 20 of flexible support fingers 22 and 24 have facing support surfaces 28 and 30 which face one another across gap 26, as can best be seen in FIG. 4. Support surfaces 28 and 30 include indentations 32 which define a shelf which is adapted to grasp and hold a wound clip. Shelves 32 are constructed and arranged so that saddle-like reinforcing members 115 of wound clips 12 can be placed in shelves 32 in such a way that wound clips 12 are held securely but can be removed readily by the user with an appropriate instrument. Shelves 32 have a horizontal ledge 34 and a vertical wall 36. The lower portions of support surfaces 28 and 30 are closer to each other than the portions of support surfaces 28 and 30 which are located above shelves 32.

Figure 3:
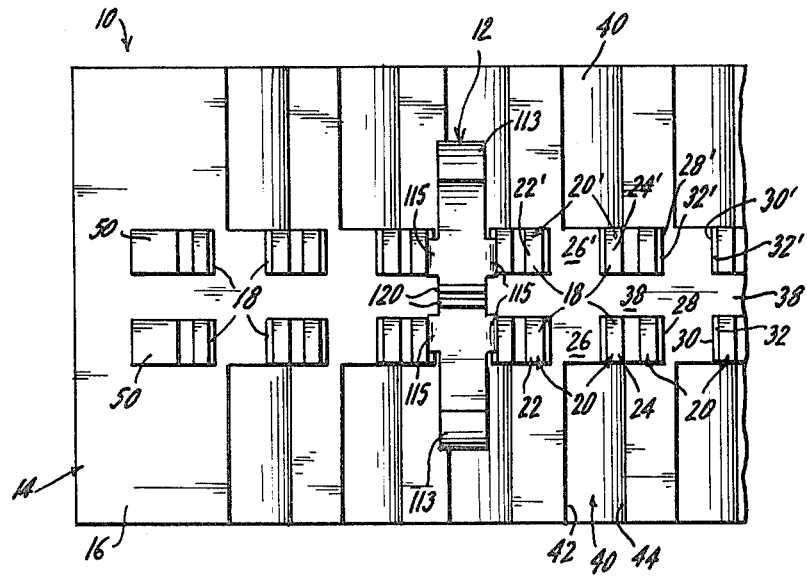
FIG. 3 is an enlarged broken top view of the rack, similar to FIG. 1, showing how a single wound clip is mounted on the rack.

As best illustrated in FIGS. 2 and 3, pairs 20 and 20' are spaced apart from each other by space 38. Support surfaces 28' and 30' of pair 20' are coplanar with and congruent to support surfaces 28 and 30 respectively of pair 20. Similarly, support surfaces 28' and 30' have shelves 32' congruent to and aligned with shelf 32 of pair 20. Shelves 32 and 32' thus support reinforced saddle-like members 115 of wound clip 12 in a symmetrical and balanced manner.

As can best be seen in FIGS. 2, 3, and 4, grooves 40 are formed in top surface 16 of base 14. Grooves 40 are substantially parallel to support surfaces 28, 30, 28' and 30', and extend from both sides of group 18 of flexible support fingers to the edge of base 14.

As illustrated in FIG. 4, groove 40 is not located symmetrically with respect to group 18, but rather is offset to one side. As will be described below, this departure from symmetry gives the rack 10 a specific loading orientation.

Groove 40 has a first end 42 defining a corner which is substantially aligned with gap 26, and a second end 44 which is positioned offset from the center of gap 26. Second end 44 preferably has a cut-away portion which can be curved and which can also be formed on an angle. Groove 40 need not have a cut-away portion but must be of sufficient depth at second end 44 to allow clearance for prongs 112 when wound clip 12 is initially inserted into position. Groove 40 must be sufficiently deep at first end 42 to fully accommodate prongs 112 when wound clip 12 is fully inserted.

As shown in FIG. 2, the plurality of support groups 18 are preferably arranged in a straight row along the center of base 14, which is elongated. Consequently, the rack 10 has a substantially rectangular shape as viewed from the top (see FIG. 1). However, for reasons to be described below, it is desirable and preferable to add at least one orientation means 46 to one end of base 14 of rack 10. As can be seen in FIG. 1, orientation means 46 can be a notched corner in an otherwise rectangular shape.

It will be readily appreciated that with the exception of the first and last support group 18 on rack 10, the flexible support finger 22 from one support group 18 will normally be in a back-to-back relationship with the flexible support finger 24 of an adjacent support group 18. Consequently, if one wishes to decrease the flexibility of the flexible support fingers and increase their rigidity, it is possible to join the bottoms of the flexible support fingers with connecting portions 48. If this is done, it will be readily understood that the first and last support groups 18 in the row will not have a support group on one side to which it can be connected. Therefore, dummy members 50 are provided at each end of a row of support groups 18 and are joined to the adjacent flexible support fingers.

The wound clips 12 can be mounted to rack 10 in a two-step process. As illustrated in FIG. 4, wound clip 12 can be first inserted on an angle as depicted on the left-hand side of FIG. 4. While the wound clip is in this position, only one side of saddle-like reinforcing members 115 of wound clip 12 rests in shelf 32 of support surfaces 28 and 28'. The other side of saddle-like reinforcing members 115 will, in this initial stage, rest against the upper portion of support surfaces 30 and 30'. In this first position, upset tabs 120 are accommodated in space 38 between pairs 20 and 20' of flexible support fingers. As previously mentioned, second end 44 of groove 40 is of sufficient depth to accommodate prongs 112 at this stage.

To complete the insertion, the wound clip 12 is rotated in a clockwise direction (as seen in FIG. 4) about the side of saddle-like reinforcing member 115 which is already resting in shelf 32 of support surfaces 28 and 28'. When the wound clip 12 is so rotated, prongs 112 sweep downward and to the left from a position near offset second end 44 of groove 40 to a position near corner 42 of groove 40. As indicated above, second end 44 of groove 40 must be of sufficient depth to allow prongs 112 to enter grooves 40. The other side of saddle-like reinforcing member 115 will then snap into shelf 32 of support surfaces 30 and 30', thus releasably securing the wound clip 12 in rack 10.

It will be readily appreciated that when the wound clip rack is constructed as illustrated in the preferred embodiment herein, the rack 10 has a loading orientation whereby wound clips 12 can best be inserted in a "clockwise" direction when viewed as in FIG. 4. This is a consequence of groove 40 being offset with respect to pair 20 of flexible support fingers. Since it is desirable to be able to load the rack 10 with wound clips 12 without close and constant visual surveillance, it is necessary that rack 10 be capable of proper orientation by the loader by some means other than appearance, so that the loader can know which way the wound clips 12 must be inserted and subsequently rotated into position. This is accomplished by means of orientation means 46 in base 14 which defines the loading orientation and which preferably can be identified tactually. It will be appreciated that when orientation means 46 can be tactually identified, wound clip racks 10 can readily be loaded with wound clips 12 without visual surveillance of the loading process.

As can be seen in FIGS. 2 and 5, a preferred wound clip rack 10 has grooves 40 of sufficient width so that wound clips 12 of varying widths can be accommodated on the same rack 10. FIG. 1 illustrates a rack having wound clips 12 of widths which decrease from left to right. FIG. 5 shows a wound clip rack 10 loaded with a wound clip 12 of one width with a wound clip 12' of a different width shown in phantom. While an individual wound clip rack of this invention can unquestionably be loaded with wound clips of different widths, it is expected that loaded racks of wound clips will typically contain wound clips of only one width on each rack. However, it will not be necessary to produce many different racks for wound clips of different widths, which will result in considerable savings of tooling time and money. As seen in FIG. 5, wound clips 12 of various widths can be accommodated in rack 10 with the end of prongs 112, 112' safely stored in grooves 40, so that they cannot accidentally cause harm to those handling a loaded rack of wound clips.

When a rack 10 has been fully loaded with wound clips 12, as illustrated schematically in FIG. 1, all but a very small portion of wound clips 12 are exposed to the atmosphere. The only portions of wound clip 12 which make contact with rack 10 are four points of the saddle-like reinforcing members 115. Consequently, once a rack 10 of wound clips 12 has been loaded, the entire rack of wound clips can be sterilized at once, since it will be possible for the sterilizing medium to reach virtually every area of the wound clips 12, including the underside and prongs 112, which are most likely to come in contact with the skin.

If the clips are to be sterilized after mounting, rack 10 must be formed from a material which itself is sanitary and which can be exposed without damage to sterilizing gases having various thermal and chemical characteristics. It will also be appreciated that the material to be used must be sufficiently flexible so that flexible members 22, 24, 22' and 24' will bend sufficiently when a wound clip 12 is wedged into it, will snap into a secure holding position after the wound clip has been rotated into position, and will yield when a wound clip is intentionally removed from the rack. It has been found that white Delrin has all the desired characteristics for such a rack.

As will be readily apparent to those skilled in the art, the invention may be used in other specific forms of wound clip racks without departing from its spirit or essential characteristics. The present embodiments are, therefore, to be considered as illustrative and not restrictive, the scope of the invention being indicated by the claims rather than the foregoing description, and all changes which come within the meaning and range of equivalents of the claims are therefore intended to be embraced therein.

We claim:

1. A rack adapted to support and dispense wound clips of the type having prongs comprising: a base having a substantially flat upper surface; a plurality of clusters of flexible support fingers projecting upwardly from and positioned above said upper surface of said base, each of said clusters adapted to support one wound clip and including at least one pair of flexible support fingers having facing support surfaces defining a space therebetween, each of said facing support surfaces having indentations positioned above said upper surface of said base and above at least a portion of said space, said indentations constructed and arranged to releasably grasp and hold a wound clip above said upper surface of said base; and groove means constructed in said base and positioned below said upper surface of said base, said groove means being positioned proximate each of said clusters and constructed and arranged to receive the prongs of the wound clips, at least a portion of said groove means being aligned between the pair of flexible support fingers of the corresponding clusters.

2. The rack of claim 1 wherein said groove means are positioned offset with respect to said at least one cluster.

3. The rack of claim 1 wherein said support fingers are positioned in back-to-back relationship with the fingers of the adjacent cluster of fingers.

4. The rack of claim 1 wherein said indentations include a substantially horizontal ledge and a substantially vertical wall.

5. In combination, a plurality of wound clips of the type having prongs and a rack adapted to support and dispense said wound clips, said rack including: a base, a plurality of clusters of flexible support fingers projecting upwardly from said base, each of said clusters adapted to support one wound clip and including at least one pair of flexible support fingers having facing support surfaces, each of said facing support surfaces having indentations releasably grasping and holding a wound clip; and groove means in said base associated with each of said clusters receiving the prongs of the wound clips, at least a portion of said groove means being situated between the pair of flexible support fingers of a corresponding cluster.

6. The combination of claim 5 wherein said wound clips include reinforcing members and wherein said reinforcing members of said wound clips are received and grasped in said indentations of said rack.

7. The method of loading a wound clip of the type having prongs in a rack adapted to support and dispense said wound clips, said rack including a base, a plurality of clusters of flexible support fingers projecting upwardly from said base, each of said clusters adapted to support one wound clip and including at least one pair of flexible support fingers having facing support surfaces, each of said facing support surfaces having indentations constructed and arranged to releasably grasp and hold a wound clip, and groove means in said base associated with each of said clusters constructed and arranged to receive the prongs of the wound clip, at least a portion of said groove means being situated between the pair of flexible support fingers of the corresponding cluster, said method comprising: first inserting said wound clip on an angle with respect to said base so that one side of said wound clip is received in the indentation of one of said support surfaces while the other side of said wound clip abuts the portion of the facing support surface at a location above the indentation in said facing support surface, and then rotating said wound clip about said one side until said other side of said wound clip snaps into said indentation on said facing support surface.

* * * * *